(12) United States Patent
Guzman (10) Patent No.: US 11,471,319 B2
(45) Date of Patent: Oct. 18, 2022

(54) SNORE BLOCKING HELMET

(71) Applicant: Cherlouise Guzman, Valencia, CA (US)

(72) Inventor: Cherlouise Guzman, Valencia, CA (US)

( * ) Notice: Subject to any disclaimer, the term of this patent is extended or adjusted under 35 U.S.C. 154(b) by 941 days.

(21) Appl. No.: 16/253,658

(22) Filed: Jan. 22, 2019

(65) Prior Publication Data

US 2020/0229965 A1   Jul. 23, 2020

(51) Int. Cl.

| | |
|---|---|
| A61F 5/56 | (2006.01) |
| A42B 1/245 | (2021.01) |
| A42B 1/242 | (2021.01) |
| A42B 1/008 | (2021.01) |
| A61M 16/00 | (2006.01) |
| A61M 16/06 | (2006.01) |
| A42B 3/04 | (2006.01) |
| A42B 3/12 | (2006.01) |
| A42B 3/22 | (2006.01) |
| A42B 3/28 | (2006.01) |
| A62B 18/04 | (2006.01) |

(52) U.S. Cl.
CPC ............... *A61F 5/56* (2013.01); *A42B 1/008* (2013.01); *A42B 1/242* (2013.01); *A42B 1/245* (2013.01); *A42B 3/044* (2013.01); *A42B 3/125* (2013.01); *A42B 3/222* (2013.01); *A42B 3/286* (2013.01); *A61M 16/0066* (2013.01); *A61M 16/022* (2017.08); *A61M 16/0627* (2014.02); *A62B 18/045* (2013.01); *A61M 2205/3584* (2013.01); *A61M 2205/587* (2013.01)

(58) Field of Classification Search
CPC ........... A61F 5/56; A42B 3/044; A42B 3/286; A61M 16/022; A62B 18/045
See application file for complete search history.

(56) References Cited

U.S. PATENT DOCUMENTS

| | | | |
|---|---|---|---|
| 3,621,488 A | 11/1971 | Gales | |
| 4,103,359 A | 8/1978 | Rieppel | |
| D255,283 S | 6/1980 | Piche | |
| 6,148,820 A | 11/2000 | Herrin | |
| 9,866,932 B2 | 1/2018 | Chang | |
| 2007/0033029 A1 | 2/2007 | Sakawaki | |
| 2007/0113324 A1* | 5/2007 | Chen | A42B 3/044 2/424 |
| 2008/0120765 A1 | 5/2008 | Zhu | |
| 2010/0095439 A1* | 4/2010 | Nolan | A42B 3/286 2/15 |

(Continued)

*Primary Examiner* — Tajash D Patel (57) ABSTRACT

A snore blocking helmet for comfortably minimizing snore impact on others includes a helmet body having a front portion, a rear portion, a right portion, a left portion, a top portion and a bottom perimeter forming an inside. The front portion has a visor aperture and a plurality of vent apertures extending through to the inside. A visor is rotatably coupled to the helmet body to cover and alternatively uncover the visor aperture. A plurality of fans is coupled within the inside adjacent the plurality of vent apertures. A control housing is coupled through the front portion. A plurality of controls is coupled to the control housing and is in operational communication with the plurality of fans. A power source is coupled to the control housing and is in operational communication each of the plurality of controls and the plurality of fans.

15 Claims, 6 Drawing Sheets

(56) References Cited

U.S. PATENT DOCUMENTS

| | | | |
|---|---|---|---|
| 2011/0231977 A1* | 9/2011 | Rupnick | A42B 3/286 454/239 |
| 2017/0157435 A1 | 6/2017 | Choi | |
| 2022/0023677 A1* | 1/2022 | Chen | A62B 18/003 |
| 2022/0095736 A1* | 3/2022 | Henshaw | A42B 3/225 |

* cited by examiner

SNORE BLOCKING HELMET

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to snore reduction devices and more particularly pertains to a new snore reduction device for comfortably minimizing snore impact on others.

BRIEF SUMMARY OF THE INVENTION

An embodiment of the disclosure meets the needs presented above by generally comprising a helmet body having a front portion, a rear portion, a right portion, a left portion, a top portion and a bottom perimeter forming an inside. The front portion has a visor aperture extending through to the inside and a plurality of vent apertures extending through to the inside. A visor is rotatably coupled to each of the right portion and the left portion to cover and alternatively uncover the visor aperture. A plurality of fans is coupled within the inside adjacent the plurality of vent apertures. A padding is coupled within the inside. A control housing is coupled through the front portion. A plurality of controls is coupled to the control housing and is in operational communication with the plurality of fans. A power source is coupled to the control housing and is in operational communication each of the plurality of controls and the plurality of fans.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 6 thereof, a new snore reduction device embodying the principles and concepts of an embodiment of the disclosure and generally designated by the reference numeral 10 will be described.

As best illustrated in FIGS. 1 through 6, the snore blocking helmet 10 generally comprises a helmet body 12 having a front portion 14, a rear portion 16, a right portion 18, a left portion 20, a top portion 22 and a bottom perimeter 24 forming an inside 26. The front portion 14 has a visor aperture 28 extending through to the inside 26 and a plurality of vent apertures 30 extending through to the inside 26. The plurality of vent apertures 30 may be horizontal slots. The helmet body 12 may be cylindrical from the front portion 14 to the rear portion 16 and from the right portion 18 to the left portion 20 with the top portion 22 being hemispherical. The front portion 14 is configured to extend down to a user's chest and the rear portion 16 is configured to extend down to a user's back. The bottom perimeter 24 has a left shoulder cutout 32 extending up the left portion 20 of the helmet body to receive a user's left shoulder and a right shoulder cutout 34 extending up the right portion 18 of the helmet body to receive a user's right shoulder. The bottom perimeter 24 may have a padded lip 36. A visor 38 is rotatably coupled to each of the right portion 18 and the left portion 20 to cover and alternatively uncover the visor aperture 28. A padding 40 is continuously coupled to the inside of the helmet body for comfort and sound dampening.

A plurality of fans 42 is coupled within the inside 26 adjacent the plurality of vent apertures 30. The plurality of fans 40 may be a pair of fans. A pair of breathing lines 44 may be coupled to the helmet body 12 through the front portion 14. The pair of breathing lines 44 comprises an intake tube 46 and an exhaust tube 48 extending through to the inside 26. The intake tube 46 is configured to receive an oxygen supply line and the exhaust tube 48 is configured to receive a CO2 exhaust line. A control housing 50 is coupled through the front portion 14 between the pair of fans 42 and above the pair of breathing lines 44. The control housing 50 may be rectangular prismatic and have a right side 52, a top side 54, a left side 56, a bottom side 58, and a front face 60. A plurality of controls 62 is coupled to the front face 60 of the control housing and is in operational communication with the plurality of fans 42. A power source 64 is coupled to the control housing 50 and is in operational communication each of the plurality of controls 62 and the plurality of fans 42. A CPU 66 is coupled to the control housing 50 and is in operational communication with the plurality of controls 62.

A Bluetooth chip 68 may be coupled to the control housing 50 and is in operational communication with the CPU 66. The Bluetooth chip 68 is configured to connect to a personal electronic device to receive audio. A pair of speakers 70 is coupled to each of the left portion 20 and the right portion 18 within the inside 26 of the helmet body. The pair of speakers 70 is in operational communication with the CPU 66, the plurality of controls 62, and the power source 64 to play audio received by the Bluetooth chip 68. A plurality of LED lights 71 may be coupled to the helmet body 12 adjacent the visor aperture 28. The plurality of LED lights 71 is in operational communication with each of the CPU 66, the plurality of controls 62 and the power source 64.

A sound detector 72 may be coupled to the control housing 50 and is in operational communication with the CPU 66. The sound detector 72 is configured to detect loudness of snoring. A vibrator 74 is coupled to the rear portion 16 adjacent the top portion 22 within the inside 26 of the helmet body. The vibrator 74 is in operational communication with the sound detector 72 and the power source 64.

Figure 1:
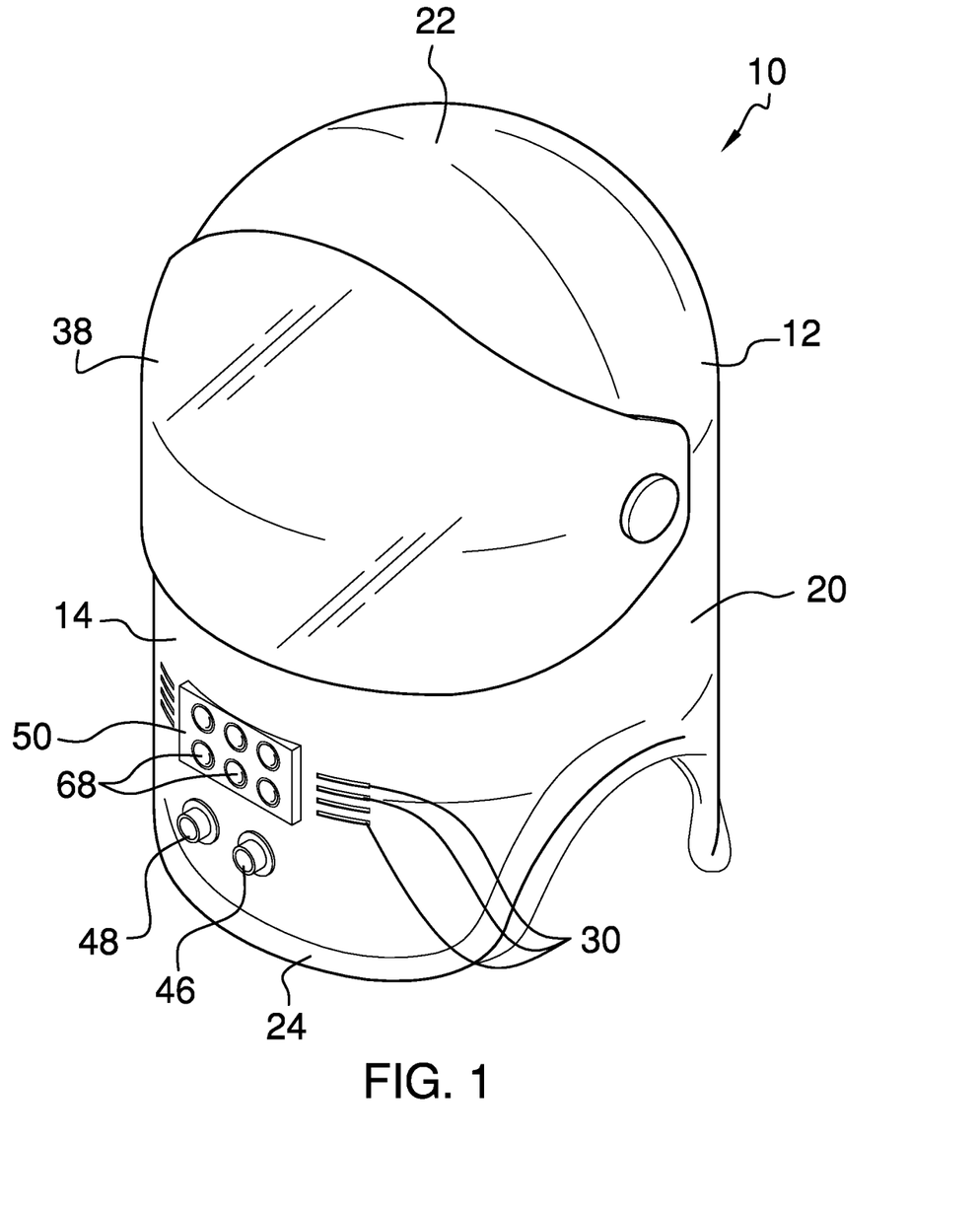
FIG. 1 is an isometric view of a snore blocking helmet according to an embodiment of the disclosure.
Figure 2:
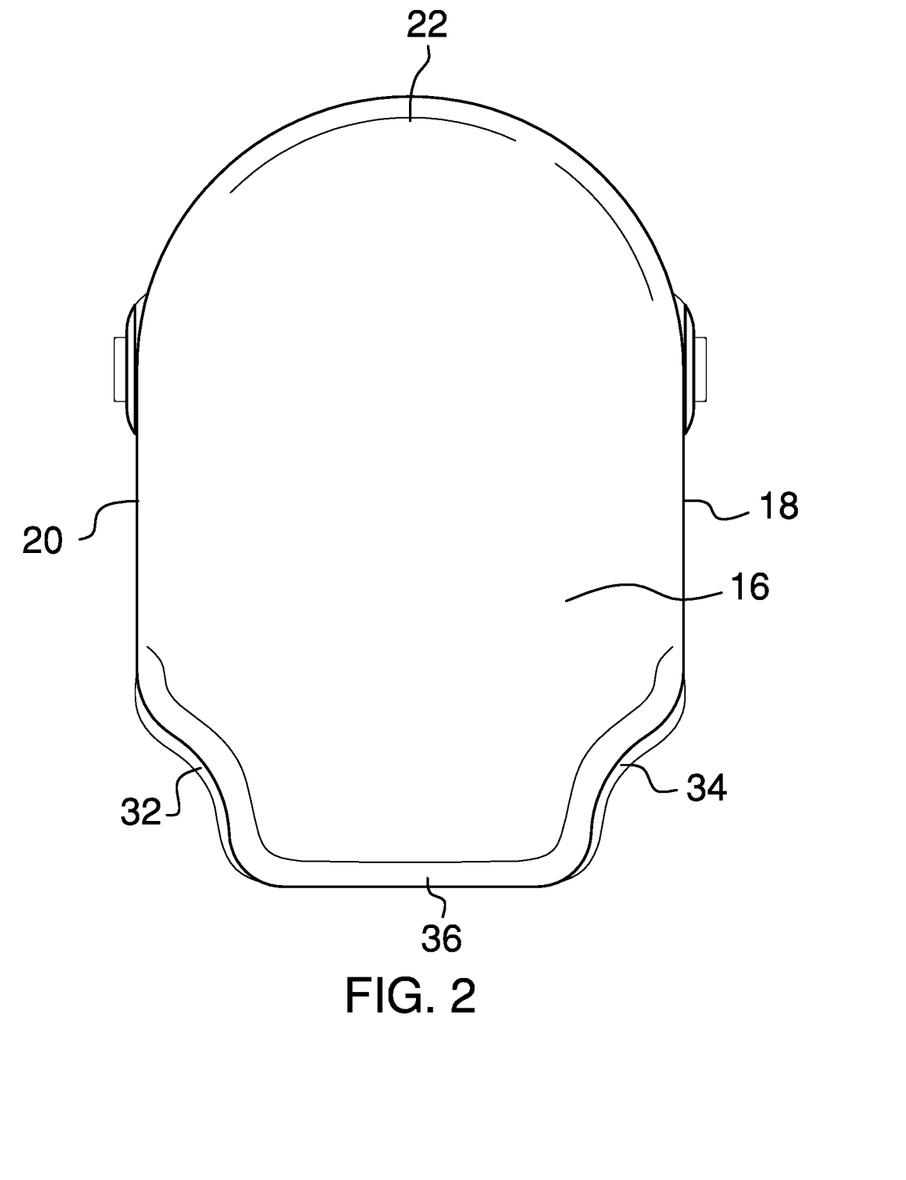
FIG. 2 is a rear elevation view of an embodiment of the disclosure.
Figure 3:
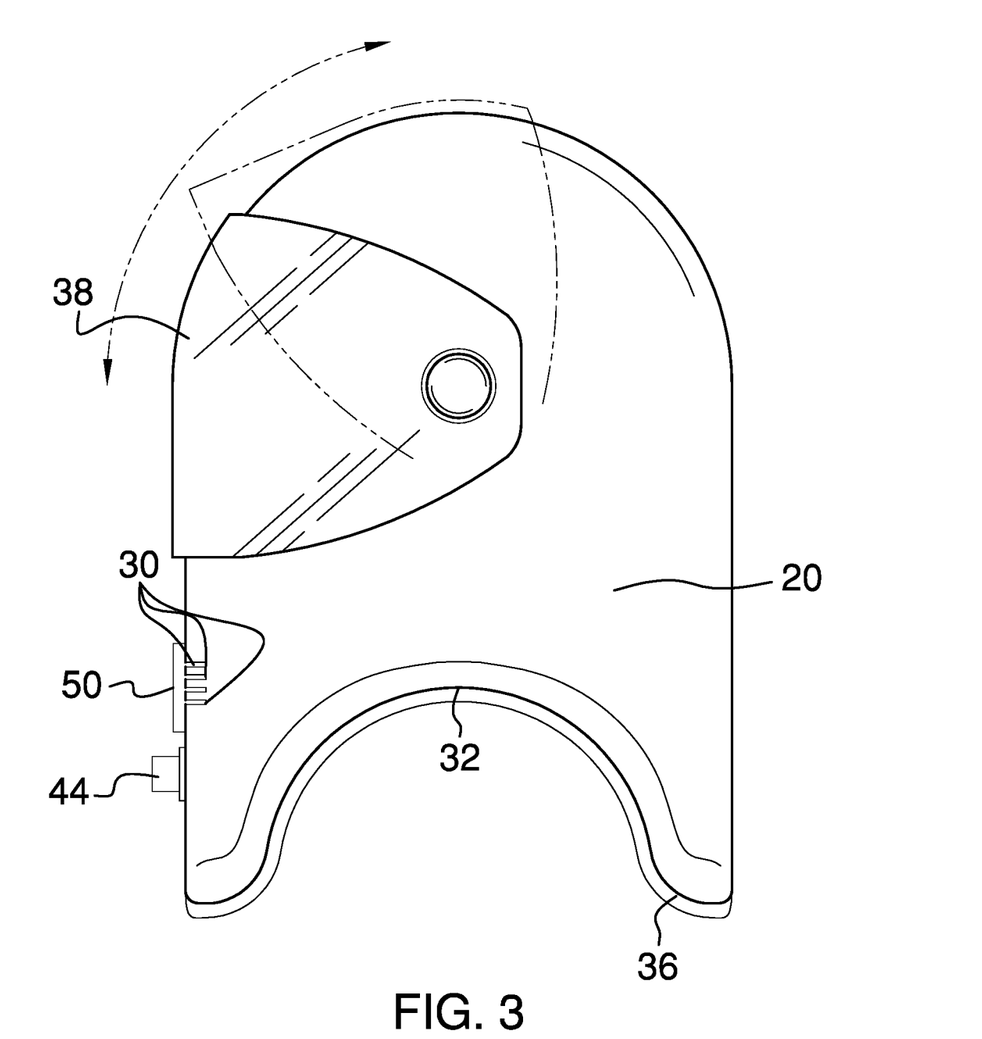
FIG. 3 is a side elevation view of an embodiment of the disclosure.
Figure 4:
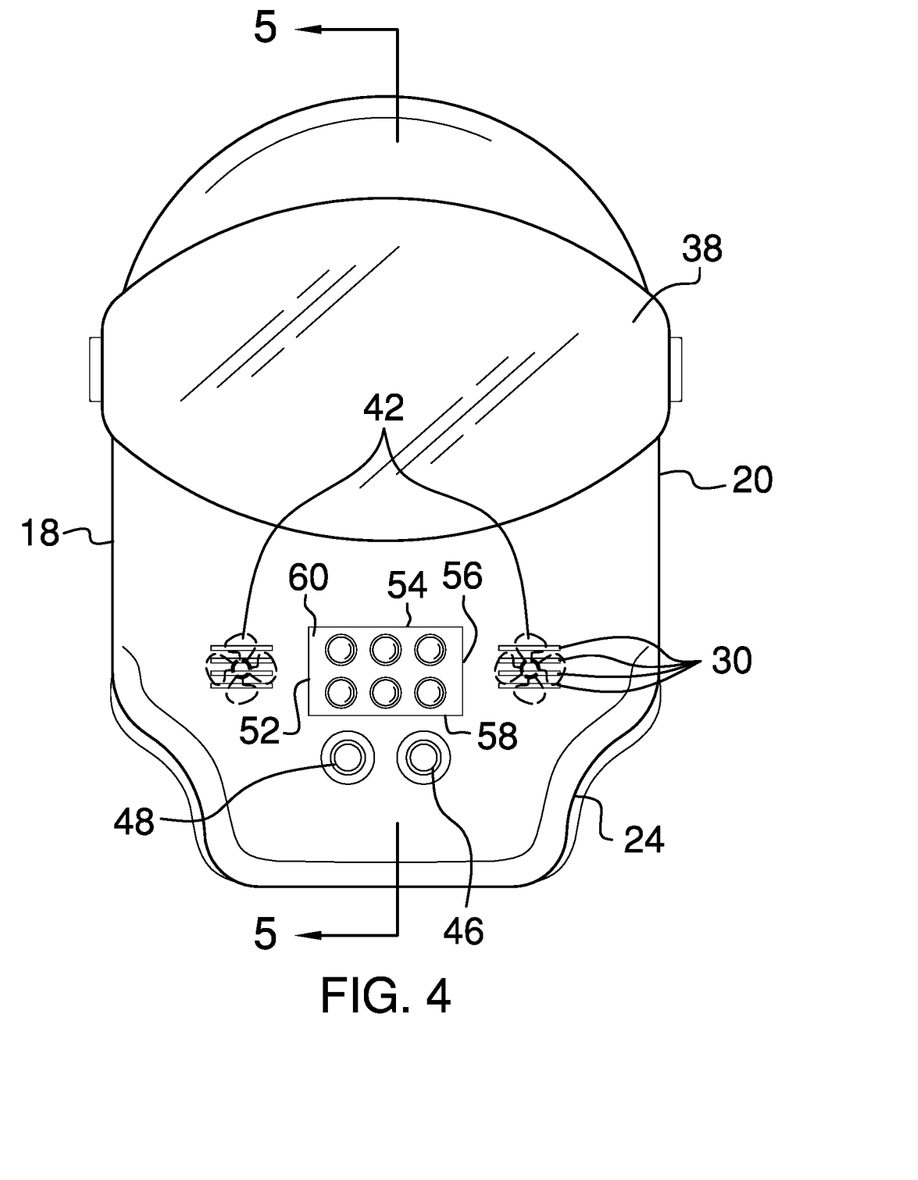
FIG. 4 is a front plan view of an embodiment of the disclosure.
Figure 5:
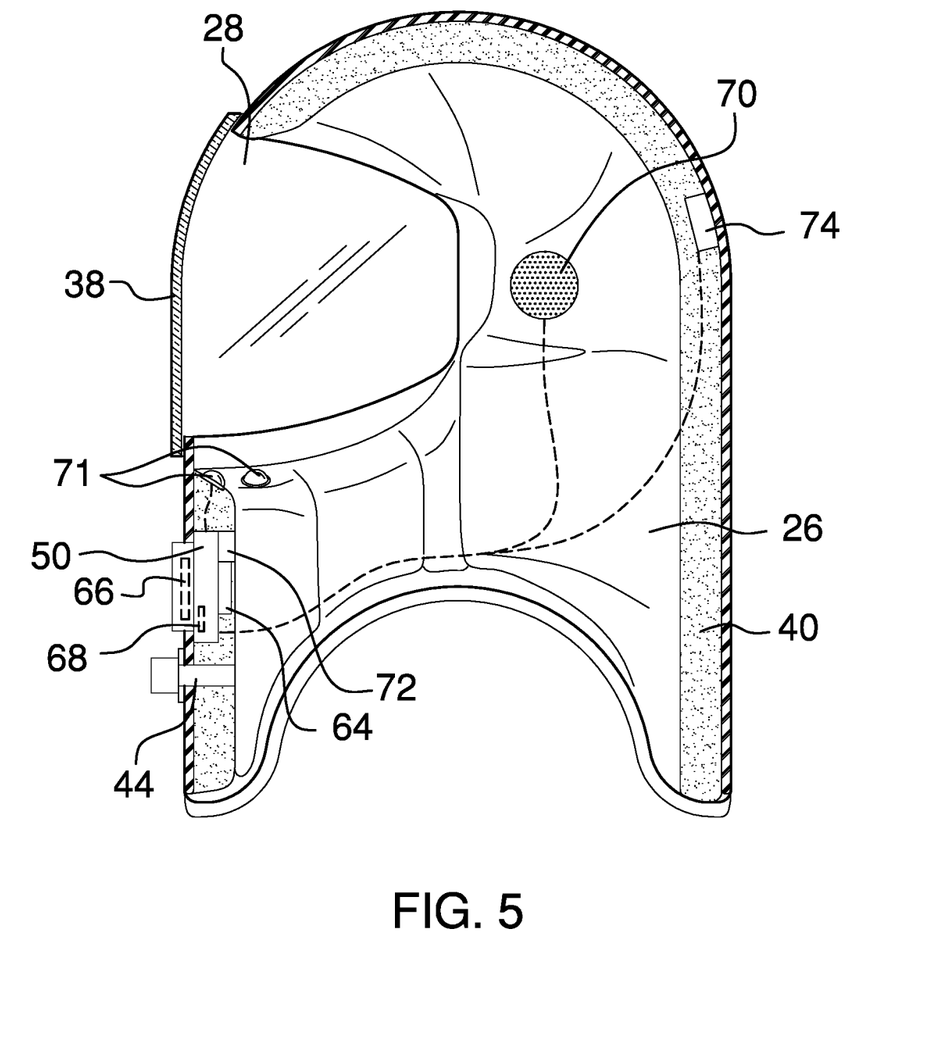
FIG. 5 is a cross-sectional view of an embodiment of the disclosure along line 5-5 of FIG. 4.
Figure 6:
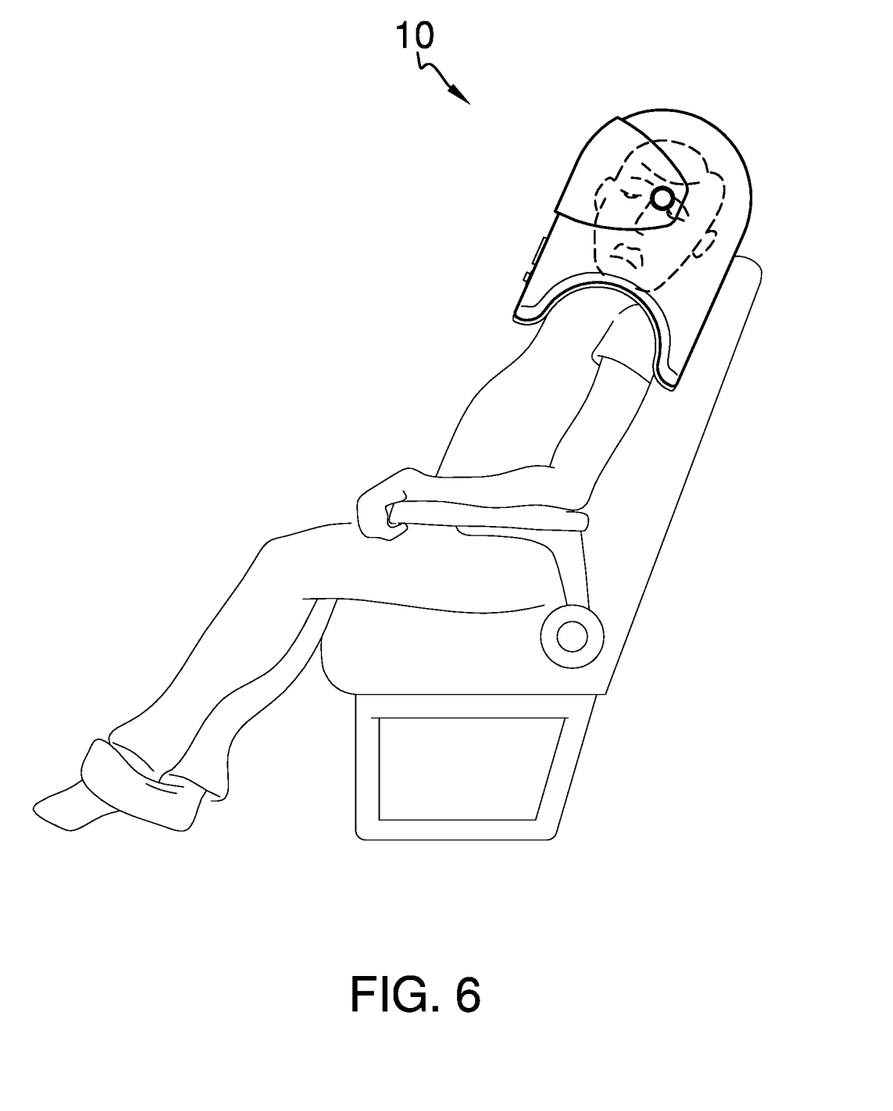
FIG. 6 is an in-use view of an embodiment of the disclosure.

In use, the helmet body 12 is worn by the user to comfortably insulate the sound of her snoring from other people, particularly while traveling. The plurality of fans 42 may be activated with the plurality of controls 62 to keep cool and music may be played over the pair of speakers 70 via the Bluetooth chip 68. The pair of breathing lines 44 may be attached to create continuous positive airway pressure without the discomfort of having to wear a face mask while sleeping. The CPU 66 activates the vibrator 74 when the sound detector reaches a threshold of loudness of snoring to gently wake the user.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A snore blocking helmet comprising:
   a helmet body, the helmet body having a front portion, a rear portion, a right portion, a left portion, a top portion and a bottom perimeter forming an inside, the front portion having a visor aperture extending through to the inside, the front portion having a plurality of vent apertures extending through to the inside;
   a visor coupled to the helmet body, the visor being rotatably coupled to each of the right portion and the left portion, the visor covering and alternatively uncovering the visor aperture;
   a plurality of fans coupled to the helmet body, the plurality of fans being coupled within the inside adjacent the plurality of vent apertures;
   a padding coupled to the helmet body, the padding being coupled within the inside;
   a control housing coupled to the helmet body, the control housing being coupled through the front portion;
   a plurality of controls coupled to the control housing, the plurality of controls being in operational communication with the plurality of fans; and
   a power source coupled to the control housing, the power source being in operational communication each of the plurality of controls and the plurality of fans.

2. The snore blocking helmet of claim 1 further comprising the helmet body being cylindrical from the front portion to the rear portion and from the right portion to the left portion, the top portion being hemispherical.

3. The snore blocking helmet of claim 2 further comprising the front portion being configured to extend down to a user's chest and the rear portion being configured to extend down to a user's back, the bottom perimeter having a left shoulder cutout extending up the left portion of the helmet body to receive a user's left shoulder and a right shoulder cutout extending up the right portion of the helmet body to receive a user's right shoulder.

4. The snore blocking helmet of claim 3 further comprising the bottom perimeter having a padded lip.

5. The snore blocking helmet of claim 1 further comprising a CPU, a Bluetooth chip, and a pair of speakers coupled to the helmet body, the CPU and the Bluetooth chip being coupled to the control housing, the Bluetooth chip being in operational communication with the CPU, the pair of speakers being coupled to each of the left portion and the right portion within the inside of the helmet body, the pair of speakers being in operational communication with the CPU, the plurality of controls, and the power source, the CPU being in operational communication with the plurality of controls.

6. The snore blocking helmet of claim 5 further comprising a plurality of LED lights coupled to the helmet body, the plurality of LED lights being in operational communication with each of the CPU, the plurality of controls, and the power source.

7. The snore blocking helmet of claim 6 further comprising the plurality of LED lights being coupled adjacent the visor aperture.

8. The snore blocking helmet of claim 5 further comprising a sound detector coupled to the control housing and a vibrator coupled to the helmet body within the inside, the sound detector being in operational communication with the CPU, the vibrator being in operational communication with the sound detector and the power source, the sound detector being configured to detect loudness of snoring, the CPU activating the vibrator when the sound detector reaches a threshold of loudness of snoring.

9. The snore blocking helmet of claim 8 further comprising the vibrator being coupled to the rear portion adjacent the top portion.

10. The snore blocking helmet of claim 1 further comprising the control housing being rectangular prismatic and having a right side, a top side, a left side, a bottom side, and a front face, the plurality of controls being coupled to the front face.

11. The snore blocking helmet of claim 10 further comprising the plurality of fans being a pair of fans, the pair of fans being coupled proximal the right side and the left side of the control housing.

12. The snore blocking helmet of claim 11 further comprising the plurality of vent apertures being horizontal slots.

13. The snore blocking helmet of claim 1 further comprising a pair of breathing lines coupled to the helmet body, the pair of breathing lines comprising an intake tube and an exhaust tube extending through to the inside, the intake tube being configured to receive an oxygen supply line and the exhaust tube being configured to receive a CO2 exhaust line.

14. The snore blocking helmet of claim 1 further comprising the pair of breathing lines being coupled through the front portion beneath the control housing.

15. A snore blocking helmet comprising:
- a helmet body, the helmet body having a front portion, a rear portion, a right portion, a left portion, a top portion and a bottom perimeter forming an inside, the front portion having a visor aperture extending through to the inside, the front portion having a plurality of vent apertures extending through to the inside, the plurality of vent apertures being horizontal slots, the helmet body being cylindrical from the front portion to the rear portion and from the right portion to the left portion, the top portion being hemispherical, the front portion being configured to extend down to a user's chest and the rear portion being configured to extend down to a user's back, the bottom perimeter having a left shoulder cutout extending up the left portion of the helmet body to receive a user's left shoulder and a right shoulder cutout extending up the right portion of the helmet body to receive a user's right shoulder, the bottom perimeter having a padded lip;
- a visor coupled to the helmet body, the visor being rotatably coupled to each of the right portion and the left portion, the visor covering and alternatively uncovering the visor aperture;
- a plurality of fans coupled to the helmet body, the plurality of fans being coupled within the inside adjacent the plurality of vent apertures, the plurality of fans being a pair of fans;
- a padding coupled to the helmet body, the padding being coupled within the inside;
- a pair of breathing lines coupled to the helmet body, the pair of breathing lines being coupled through the front portion, the pair of breathing lines comprising an intake tube and an exhaust tube extending through to the inside, the intake tube being configured to receive an oxygen supply line and the exhaust tube being configured to receive a CO2 exhaust line;
- a control housing coupled to the helmet body, the control housing being coupled through the front portion between the pair of fans and above the pair of breathing lines, the control housing being rectangular prismatic and having a right side, a top side, a left side, a bottom side, and a front face;
- a plurality of controls coupled to the control housing, the plurality of controls being coupled to the front face, the plurality of controls being in operational communication with the plurality of fans;
- a power source coupled to the control housing, the power source being in operational communication each of the plurality of controls and the plurality of fans;
- a CPU, the CPU being coupled to the control housing, the CPU being in operational communication with the plurality of controls;
- a Bluetooth chip, the Bluetooth chip being coupled to the control housing, the Bluetooth chip being in operational communication with the CPU;
- a pair of speakers coupled to the helmet body, the pair of speakers being coupled to each of the left portion and the right portion within the inside of the helmet body, the pair of speakers being in operational communication with the CPU, the plurality of controls, and the power source;
- a plurality of LED lights coupled to the helmet body, the plurality of LED lights being coupled adjacent the visor aperture, the plurality of LED lights being in operational communication with each of the CPU, the plurality of controls, and the power source;
- a sound detector coupled to the control housing, the sound detector being in operational communication with the CPU, the sound detector being configured to detect loudness of snoring; and
- a vibrator coupled to the helmet body, the vibrator being coupled to the rear portion adjacent the top portion within the inside, the vibrator being in operational communication with the sound detector and the power source, the CPU activating the vibrator when the sound detector reaches a threshold of loudness of snoring.

* * * * *